(12) United States Patent
Biekle et al.

(10) Patent No.: US 8,252,535 B2
(45) Date of Patent: Aug. 28, 2012

(54) RNA INTERFERENCE TAGS

(75) Inventors: Wolfgang Biekle, Cologne (DE); Peter Hahn, Kurten (DE)

(73) Assignee: Qiagen GmbH, Hilden (DE)

( * ) Notice: Subject to any disclaimer, the term of this patent is extended or adjusted under 35 U.S.C. 154(b) by 10 days.

(21) Appl. No.: 12/529,465

(22) PCT Filed: Apr. 10, 2007

(86) PCT No.: PCT/EP2007/053459
§ 371 (c)(1),
(2), (4) Date: Sep. 1, 2009

(87) PCT Pub. No.: WO2008/122314
PCT Pub. Date: Oct. 16, 2008

(65) Prior Publication Data
US 2010/0099191 A1 Apr. 22, 2010

(51) Int. Cl.
*C12Q 1/68* (2006.01)
*C12N 15/11* (2006.01)
*C12N 5/00* (2006.01)
*C07H 21/04* (2006.01)

(52) U.S. Cl. ....... 435/6.1; 514/44 A; 536/24.5; 435/325; 435/375; 435/410

(58) Field of Classification Search .................. None
See application file for complete search history.

(56) References Cited

U.S. PATENT DOCUMENTS
2004/0234504 A1* 11/2004 Verma et al. ................. 424/93.2

FOREIGN PATENT DOCUMENTS
| DE | 102006016365 A1 | 10/2007 |
|---|---|---|
| WO | 02/44321 A2 | 6/2002 |
| WO | 2004/020631 A2 | 3/2004 |
| WO | 2005/059132 A1 | 6/2005 |

OTHER PUBLICATIONS pEGFP-N1 vector information, Catalog #6085-1, Clontech, published on Oct. 3, 2002.*
Campbell et al., Knockdown of chimeric glucocerebrosidase by green fluorescent protein-directed small interfering RNA, 2004, Genetics and Molecular Research, vol. 3, pp. 282-287.*
Wadsworth et al., Stable expression of fluorescently tagged porteins for studies of mitosis in mammalian cells, 2005, Nature Methods, vol. 2, pp. 981-987.*
"Tet-Off® and Tet-on® Gene Expression Systems User Manual", Tet Systems User Manual, Clontech Lbaoratories Inc., published on Sep. 13, 2005.*
Wiznerowicz et al., Conditional suppression of cellular genes: Lentivirus vector-mediated drug-inducible RNA interference, 2003, Journal of Virology, vol. 77, pp. 8957-8961.*
Chiu et al., siRNA function in RNAi: A chemical modification analysis, 2003, RNA, vol. 9, pp. 1034-1048.*
Makarova et al., A putative RNA-interference-based immune system in prokaryotes: computational analysis of the predicted enzymatic machinery, functional analogies with eukaryotic RNAi, and hypothetical mechanisms of action, 2006, Biologay Direct, vol. 1, Issue 7, pp. 1-26.*
Barrangou et al., CRISPR provides acquired resistance against viruses in prokaryotes, 2007, Science, vol. 315, pp. 1709-1712.*
Sheilagh Molloy, First evidence of prokaryotic RNAi? 2007, Nature Reviews Microbiology, vol. 5, p. 329.*
Makarova et al., Prokaryotic homologs of Argonaute proteins are predicted to function as key components of a novel system of defense against mobile genetic elements, 2009, Biology Direct, vol. 4, Issue 29, pp. 1-15.*
Hahn et al.; "An siRNA-based system for differential regulation of Ectopic gene expression constructs"; Journal of Biotechnology; vol. 128, No. 4; Mar. 6, 2007; pp. 762-769; XP005916237.

* cited by examiner

*Primary Examiner* — Dana Shin
(74) *Attorney, Agent, or Firm* — Rankin, Hill & Clark LLP

(57) ABSTRACT

The invention relates to a method for inhibiting the expression of a target gene in a eukaryotic cell. The method includes the following steps: a) providing at least one eukaryotic cell, the cell being capable of RNA interference, b) transfecting the eukaryotic cell with a composition that includes a genetic construct that includes an siRNA tag, and a target gene that forms a transcription unit together with the siRNA tag, and c) introducing at least one siRNA that is complementary to the siRNA tag of the transfected genetic construct to inhibit the expression of the target gene.

40 Claims, 4 Drawing Sheets

FIG. 2A

Figure 1A:
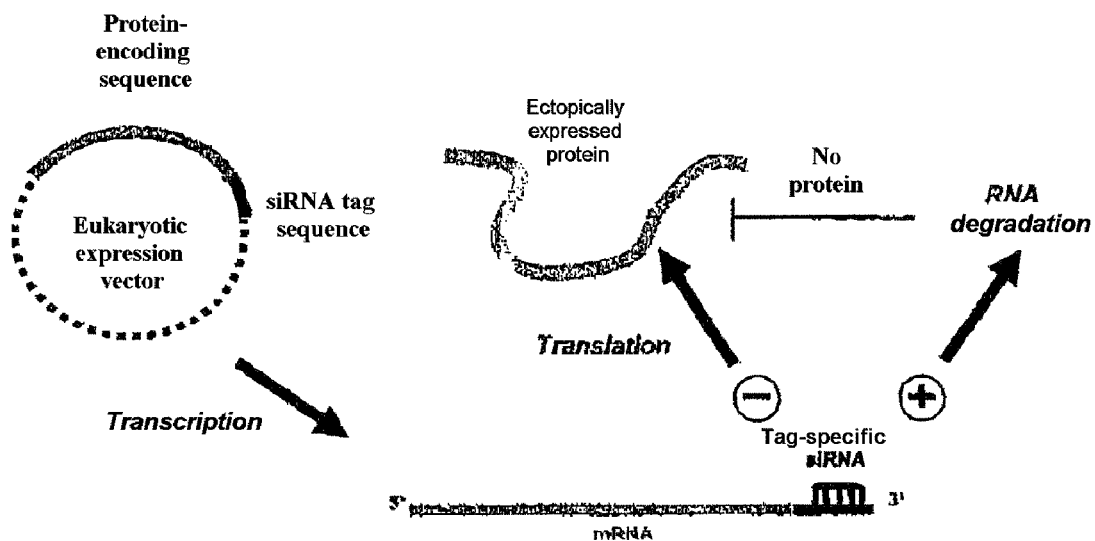

| 5' cloning site | (His) protein tag | Stop codons | siRNA tags | poly-A signal | 3' cloning site |

Oligo: 274-6

```
274-hs fwd: 5'  AATTCCACCACCATCACCATCACCATCACTAGTAATGACAGGGTATCGACCATTACAAATAATAAAG     3'
274-hs rev: 3'      GGTGGTGGTAGTGGTAGTGGTAGTGATCATTACTGTCCCATAGCTGGTAATGTTTATTATTTCCTAG   5'
```

Oligo: 1248-6

```
1248-hs fwd 5'  AATTCCACCACCATCACCATCACCATCACTAGTAATGAAAGCGTTGAAAATAGCCTACAATAATAAAG   3'
1248-hs rev 3'      GGTGGTGGTAGTGGTAGTGGTAGTGATCATTACTTTCGCAACTTTATCGGATGTTATTATTTCCTAG  5'
```

Oligo: 2904-6

```
2904-hs fwd 5'  AATTCCACCACCATCACCATCACCATCACTAGTAATGACTGGATACGCGGACGTTTAATAATAAAG    3'
2904-hs rev 3'      GGTGGTGGTAGTGGTAGTGGTAGTGATCATTACTGACCTATGCGCCTGCAAATTATTATTTCCTAG   5'
```

FIG. 2B

| 5' cloning site | Stop codons | siRNA tags | poly-A signal | 3' cloning site |

Oligo: 274-4

```
274 fwd: 5'  AATTCCTAGTAATGACAGGGTATCGACCATTACAAATAATAAAG    3'
274 rev: 3'      GGATCATTACTGTCCCATAGCTGGTAATGTTTATTATTTCCTAG   5'
```

Oligo: 1248-4

```
1248 fwd 5'  AATTCCTAGTAATGAAAGCCTTGAAAATAGCCTACAATAATAAAG   3'
1248 rev 3'      GGATCATTACTTTCGCAACTTTATCGGATGTTATTATTTCCTAG   5'
```

Oligo: 2904-4

```
2904 fwd 5'  AATTCCTAGTAATGACTGGATACGCGGACGTTAATAATAAAG      3'
2904 rev 3'      GGATCATTACTGACCTATGCGCCTGCAAATTATTATTCCTAG     5'
```

RNA INTERFERENCE TAGS

CROSS-REFERENCE TO RELATED APPLICATIONS

The present application is a U.S. National Stage application of PCT/EP2007/053,459, filed Apr. 10, 2007.

BACKGROUND OF THE INVENTION

1. Field of the Invention

The present invention relates to a composition for inhibiting the expression of one or more target genes in a eukaryotic cell by means of RNA interference, and to the use of appropriate compositions and to a method for inhibiting the expression of one or more target genes in a eukaryotic cell by means of RNA interference.

2. Description of Related Art

The phenomenon known from the literature as "RNA interference" (RNAi) is based on the fact that short RNA molecules (siRNA, small interfering RNA) can interact with messenger RNA (mRNA) in the cell (Literature: Fire A., Xu S., Montgomery M. K., Kostas S. A., Driver S. E., Mello C. C., Nature Feb. 19, 1998; 391 (6669): 744-745). A complex mechanism, which is controlled by enzymes, results in breakdown (degradation) of the mRNA, thus inhibiting the expression of the mRNA and therefore also protein expression (called gene silencing, i.e. switching off a gene or gene inactivation).

Besides siRNA, further small RNA species have been discovered, for example the micro-RNAs (miRNA) or short hairpin RNAs (shRNA), which are likewise able to inhibit protein expression by related mechanisms.

WO 02/44321 discloses the introduction of siRNA into cells in order to inhibit the expression of a gene which occurs naturally in the cells. WO 02/44321 further discloses the introduction of a foreign target gene into a cell. Expression of the introduced target gene can be inhibited by additional introduction of siRNA, which is always derived from the sequence of the introduced target gene, in the expression.

It has emerged that not every sequence is equally suitable for the RNA interference mechanism. Some criteria for the composition of an efficient siRNA have been identified. Reynolds et al. published a selected criteria in Nat. Biotechnol. March 2004, 22(3): 326-330. Electronic publication took place on Feb. 1, 2004 with the title "Rational siRNA design for RNA interference".

The conventional practice is to derive specific siRNAs individually for each gene to be inhibited from the sequence thereof. Such a procedure is time-consuming and of low efficiency because the derived siRNAs frequently prove to be unable to inhibit gene expression satisfactorily only when tested. In addition, each individual siRNA sequence entails the risk of having its own nonspecific gene regulation profiles, the so-called off-target effects.

Since the prior art discloses exclusively compositions and methods in which each siRNA is derived individually and in an elaborate manner directly from the gene to be inhibited, the object of the present invention is to make it possible to inhibit simply, efficiently and universally the expression of target genes introduced into the cell by means of RNA interference ("RNAi").

BRIEF SUMMARY OF THE INVENTION

The present invention is therefore to be seen in that the composition of the invention comprises a construct, and the target gene is introduced by means of this construct into a eukaryotic cell, where the construct includes at least one first target gene and at least one associated so-called "siRNA tag". An siRNA tag is defined herein as a genetic element which forms a transcription unit with the target gene and is specifically recognized by a complementary siRNA. The gene constructs containing the siRNA tag are thus subjected to RNA interference or another gene-inhibitory process. It is preferred according to the invention to use siRNA tags known to be able to bring about particularly potently an RNA interference in a particular cell and ideally cause minimal off-target effects.

The present invention allows in particular also simultaneous, but mutually independent, regulation of a plurality of introduced target genes by means of specifically designed siRNAs and their associated target sequences.

This object is achieved by the invention through a composition comprising a genetic construct, and the target gene is introduced by means of this construct into the eukaryotic cell, where the construct includes a first target gene and a first siRNA tag, and a method comprising transfecting at least one eukaryotic cell with such a composition, and introducing at least one siRNA that is complementary to an siRNA tag of the transfected construct. Further advantageous aspects, details and embodiments of the invention are evident from the dependent claims, the description and the figures.

The composition of the invention is thus suitable for inhibiting the expression (e.g. the ectopic expression) of one or more target genes in a eukaryotic cell by means of RNA interference and also relates to the use of corresponding compositions, and a method for inhibiting the expression of one or more target genes in a eukaryotic cell by means of RNA interference.

BRIEF DESCRIPTION OF THE DRAWING FIGURES

Figure 1B:
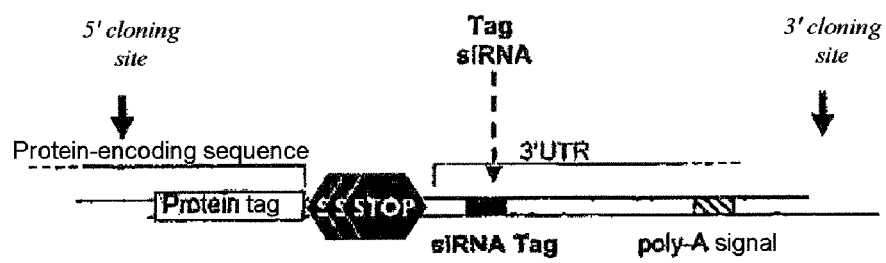
Figure 3A:
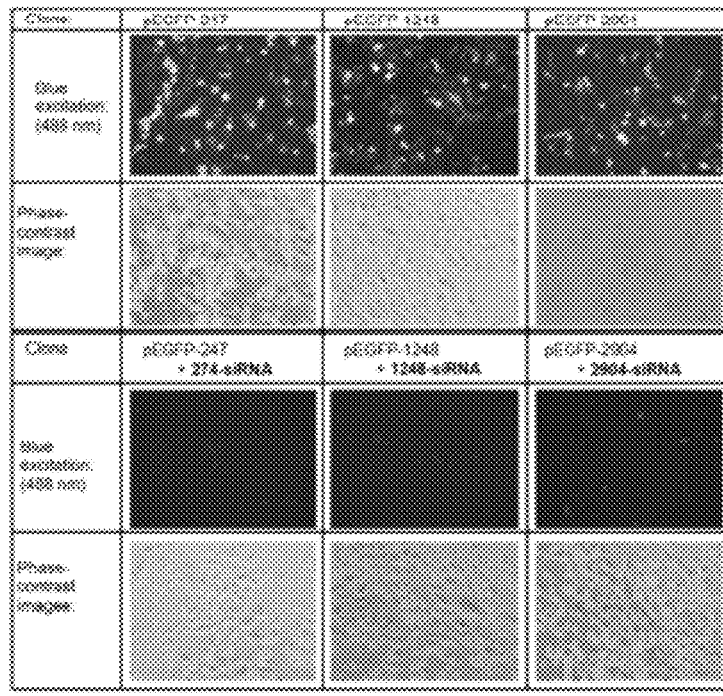
Figure 3B:
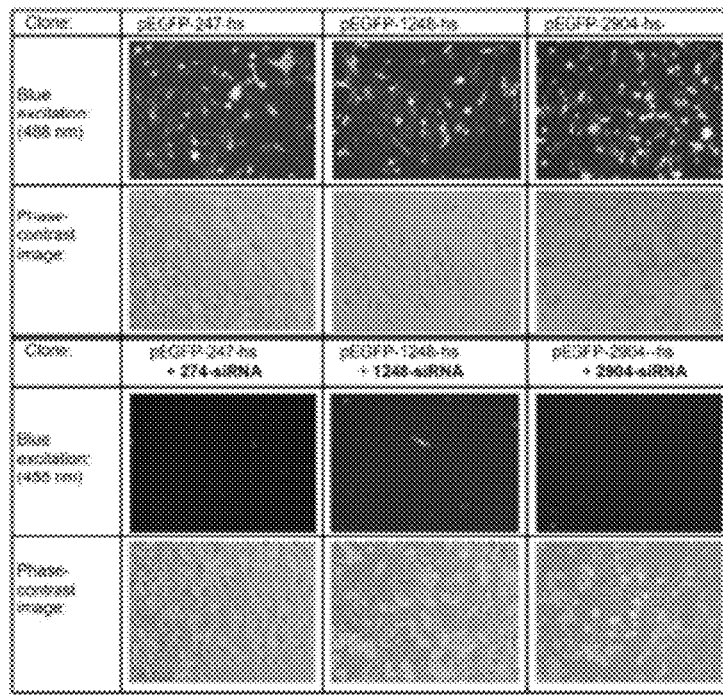
Figure 3C:
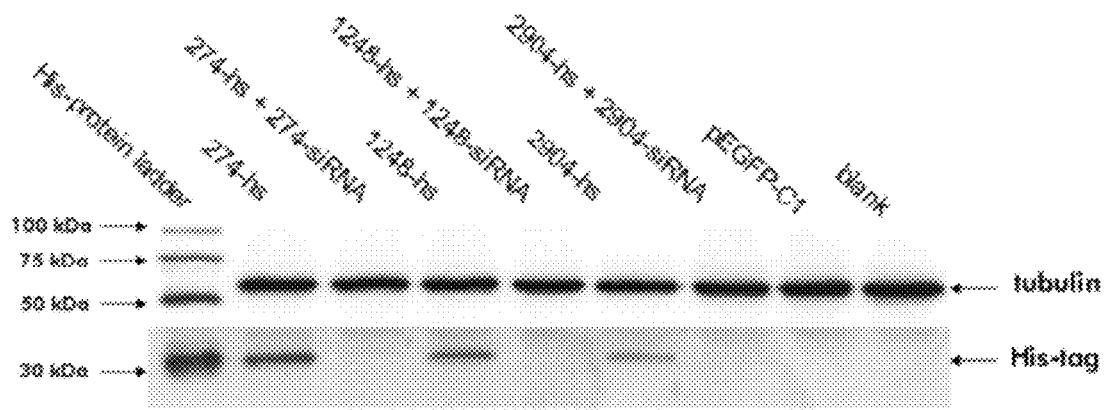
Figure 4:
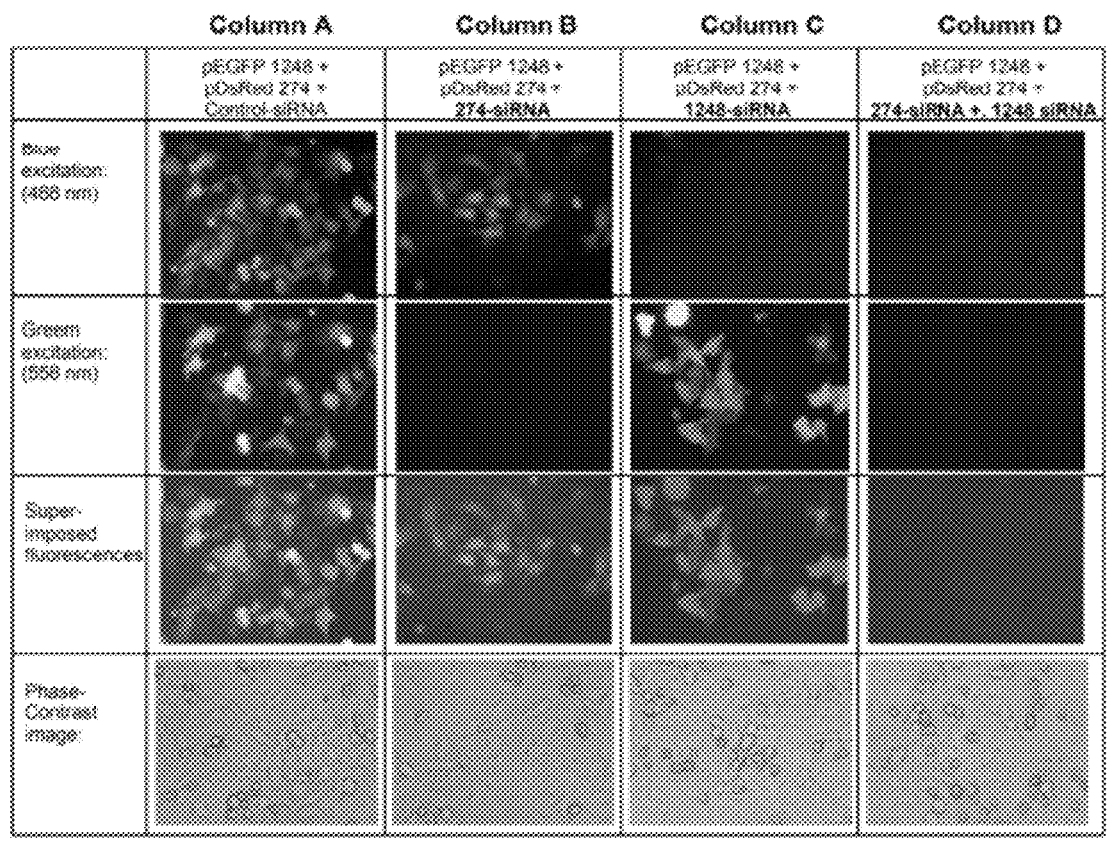

FIGS. 1A and 1B show an exemplary overview of the function and use of an siRNA tag of the invention;

FIGS. 2A and 2B show exemplary DNA cassettes comprising siRNA tag sequences suitable for cloning into a plasmid, wherein: the siRNA tag sequence for 274-hs fwd in Oligo 274-6 is SEQ ID NO:1; the siRNA tag sequence for 1248-hs fwd in Oligo 1248-6 is SEQ ID NO:2; the siRNA tag sequence for 2904-hs fwd in Oligo 2904-6 is SEQ ID NO:3; the siRNA tag sequence for 274 fwd in Oligo 274-4 is SEQ ID NO:1; the siRNA tag sequence for 1248 fwd in Oligo 1248-4 is SEQ ID NO:2; and the siRNA tag sequence for 2904 fwd in Oligo 2904-4 is SEQ ID NO:3;

FIGS. 3A to 3C show exemplary immunofluorescence images of pEGFP constructs employed with siRNA tag, in each case without and with specific siRNA; and FIG. 4 shows an example of a selective gene silencing by cotransfection of two expression plasmids comprising constructs of the invention (here with sequences coding for the fluorescent proteins EGFP and DsRed) with different siRNA tags and the respective siRNAs.

DETAILED DESCRIPTION OF THE INVENTION

Definitions siRNA means in the context of the present invention all RNA species capable of RNA interference, i.e. are able to bring about inhibition of the expression of a transcript. The inhibition normally takes place by sequence-specific recognition of an siRNA tag by the siRNA. An siRNA preferably has a 100% homology with the associated siRNA tag. However, examples in which a lower degree of homology may be sufficient for a certain inhibiting effect of an siRNAs are also known. This phenomenon may also be based on translation inhibition, as described also for the mode of action of the so-called micro-RNAs (miRNAs).

siRNA tags are sequences which are complementary to an siRNA. They form a transcription unit with the target gene and are located in the 5'-non-coding or in the 3'-non-coding region of the transcript, and/or they overlap with the coding region of the transcript. The fact that the siRNA tags are independent sequences means that they have the advantage of being universally employable. An siRNA tag may also be a constituent of an artificial or natural promoter/enhancer/silencer. The gene silencing mediated in this way is known to those skilled in the relevant art under the heading "transcriptional inhibition".

A target gene means a nucleic acid sequence which codes for a functional RNA (for example a tRNA, rRNA etc.) or a protein, the expression or translation of which is to be inhibited by means of siRNA through breakdown of the transcript.

A composition means in the context of the invention an aqueous solution comprising one or more different recombinant nucleic acids. The solution preferably comprises further constituents which make transfection of the nucleic acid possible. Corresponding compositions are sufficiently well known to the person skilled in the art from the prior art.

Many biological questions cannot be meaningfully answered by stating absolute values. It is often considerably more informative for example to compare the biological effects of an expression of genes directly. Particularly suitable for this purpose is a composition of the invention for inhibiting the expression of a target gene or a plurality of target genes in a eukaryotic cell by means of RNA interference, which is characterized in that it comprises at least two genetic constructs, and the target genes are introduced by means of these constructs into the eukaryotic cell, where (a) the first construct includes a first target gene and a first siRNA tag, and (b) the second construct includes a second target gene and a second siRNA tag, where the first and the second siRNA tag are different from one another.

It is possible through the use of two different siRNA tags to modulate the two gene expressions which are to be compared. For this purpose, two different target genes are employed on the two constructs used.

It is further advantageous to use the same target gene on two constructs in order in this way to obtain information on dose effects for the gene and for the siRNA.

A further possibility is to study two alleles of the same target gene in a cell by two constructs by means of the composition of the invention. The different siRNA tags make it possible to modulate the expression of the two alleles individually and thus obtain information about the functions of the different alleles, e.g. dominant negative forms and wild-type variants or else various splice variants.

The composition of the invention is not confined to one or two constructs. It is possible to add a third construct, a fourth construct and any number of further constructs which, besides a target gene, always comprise an siRNA tag. This makes it possible to investigate complex interactions of genes and, by introducing siRNAs, inhibit the expression of individual target genes or groups of target genes in a modulating way, in order thus to obtain pointers to the effect of the target genes or else the cellular genes.

The target genes can be fused to a marker gene for simple monitoring of the expression thereof. It is particularly advantageous to fuse different target genes to different marker genes, so that fusion proteins are expressed, making it possible to detect the individual target genes specifically. Suitable marker genes for fusion from the group of known marker genes are: (enhanced) green fluorescent protein and derivatives thereof ((E)GFP; YFP; CFP), also dsRed, Myc tag, E tag, FLAG tag, Glu-Glu tag, GST tag, HA tag, His tag, HSV tag, luciferase, MBP, protein C tag, S tag, T7 tag, V5 tag, VSV-g tag, avidin/streptavidin/strep tag, thioredoxin, His-patch thioredoxin, β-galactosidase, chloramphenicol acetyltransferase, cellulose binding domains (CBDs), chitin binding domain, staphylococcal protein A, streptococcal protein G, neo, hyg, pac, zeo, gpt, ble, dhfr, hpt and npt II. Further marker genes for fusion making detection of the target gene possible can likewise be used.

Marker genes from the group of fluorescence-generating proteins are preferably used, because detection thereof is not complicated. An advantage of this type of detection is that determination of the living cell is possible by non-invasive fluorescence measurement or fluorescence microscopy. It is particularly preferred for two distinguishable marker genes to code for different fluorescence-generating proteins which generate fluorescence differing in wavelength.

The composition of the invention allows studies on different eukaryotic cells. The cells may be for example of animal origin. It is moreover possible for the cells to remain in the animal in vivo, to be taken from an animal, to embody an animal unicellular organism or else to be derived from a cell culture with animal cells. The animal cells may be for example cells derived from a mammal (called mammalian cells).

On the other hand, the cells may also be of vegetable origin. The cells may remain in a plant in vivo, be taken from a plant, embody a plant unicellular organism or else be derived from a cell culture with plant cells.

The cell may furthermore be a fungal cell. These cells of mycotic origin include all fungi capable of RNA interference. Yeasts for example are known as model organism from the prior art. It is known from the literature that, for example, Saccharomyces spec. is not capable of RNA interference. By contrast, it is known that, for example, the fission yeast *Schizosaccharomyces pombe* is amenable to RNA interference.

The sequences selected according to the invention as siRNA tag either are not themselves a constituent of the transcript to be inhibited, or overlap only partly therewith. It has surprisingly been found that the siRNA tag need not be a constituent of the coding sequence; on the contrary, it is sufficient for efficient RNA interference that the siRNA tag is merely in fact a constituent of the transcript, meaning that it forms a transcription unit with the target gene.

Sequences advantageously used as siRNA tags are those which do not occur naturally in the cell to be transfected. They may, of course, also be sequences which are not, or currently not yet, listed in the available sequence databases. A further possibility is also to use sequences which have no correspondence in nature, and these are therefore referred to as artificial (or synthetic) sequences.

It is possible and preferable to avoid an interaction of the siRNAs directed against siRNA tags with gene products of the target cell to be transfected by deriving the sequence of the siRNA tag and thus of the siRNA from nucleic acid sequence segments which do not themselves occur in the target cell to be transfected. It is preferred for this purpose in particular for the siRNA tags of the invention to be derived from the genome of prokaryotes or archae-bacteria. These nucleic acid sequences are particularly preferably derived from the genome of archae-bacteria, for example from the genera

*Thermotoga* (e.g. *Thermotoga maritima*, etc.), *Methanosarcina* (e.g. *Methanosarcina mazei*, etc.), *Pyrococcus* (e.g. *P. furiosus, P. horikoshii, P. woesei*, etc.), *Halobacterium* (e.g. *H. cutirubrum, H. denitrificans, H. halobium*, etc.), *Methanolobus* (e.g. *M. bombayensis, M. oregonensis, M. siciliae*, etc.), *Sulfolobus* (e.g. *S. acidocaldarius, S. brierleyi, S. hakonensis*, etc.) or *Acidilobus* (e.g. *A. aceticus*). Further corresponding archae genera are known to a person skilled in the art.

The siRNA tags of the invention very particularly preferably have the sequences indicated in Table 1 and shown in context once more in FIG. 2, although the use of siRNA tags of the invention is not confined thereto. Table 1 thus shows an overview of the sequences of the three siRNA tags used herein by way of example, and of the associated siRNAs in each case.

TABLE 1

| Sequence name | siRNA sequence | siRNA tag sequence |
|---|---|---|
| Sequence 274 | 5'-GGGUAUCGACGAUUACAAAUU-3' [SEQ ID NO: 4] 3'-GUCCCAUAGCUGCUAAUGUUU-5' [SEQ ID NO: 7] | CAGGGTATCGACGATTACAAA [SEQ ID NO: 1] |
| Sequence 1248 | 5'-GCGUUGAAAUAGCGUACAAdTT-3' [SEQ ID NO: 5] 3'-dTTCGCAACUUUAUCGCAUGUU-5' [SEQ ID NO: 8] | AAGCGTTGAAATAGCGTACAA [SEQ ID NO: 2] |
| Sequence 2904 | 5'-GGAUACGCGGGACGUUUAAUU-3' [SEQ ID NO: 6] 3'-GACCUAUGCGCCCUGCAAAUU-5' [SEQ ID NO: 9] | CTGGATACGCGGGACGTTTAA [SEQ ID NO: 3] |

The siRNA tag of the composition of the invention may be located either 3'-downstream or 5'-upstream of the coding region of the mRNA whose expression is to be inhibited. As in the case of the siRNA tag located 3'-downstream and in the case of that located 5'-upstream it is possible for the siRNA tag to overlap with the sequence of the coding region. It is worthwhile for certain questions for the position of the siRNA tag to be located in an intron of the unspliced mRNA, for example in order to investigate further the selective mechanisms of the RNA interference itself.

In order to facilitate purification and also detection of the protein encoded by the target gene, the target gene is preferably fused to a peptide tag for protein purification. For example, the His tag is used for fusion to the target genes coding for proteins, because this tag is small and consists for example of 6 histidine amino acids. Purification via nickel-NTA columns is possible without complications. These nickel-NTA columns are commercially available. The composition which comprises a tag for protein purification is compatible with fusion products of target gene and marker gene. Besides the His tag, it is possible to use many other tags for protein purification, for example HA tags, ERK tags, GFP and related fusion tags, Myc tags, FLAG tags, GST tags, Strep tags, β-Gal tags, MBP tag and other tags are likewise suitable.

The cells are transfected according to the invention with a construct or a plurality of constructs. It is possible in this connection for each construct to be a constituent of its own vector, or two or more constructs can be present on one vector. It is ensured thereby that the two or more constructs are introduced into the cell in a fixed stoichiometric ratio. Plasmids are particularly suitable vectors for the constructs. It is also possible to employ transposons or viral vectors or other autonomous nucleic acids as vectors. In the simplest case, a vector is dispensed with, and the construct is part of an amplified nucleic acid, for example part of a PCR product.

The composition which comprises at least one construct is used according to the invention to make it possible to inhibit the expression of an introduced target gene in a cell. The cell is transfected with the composition for this purpose. At the same time, previously or subsequently, the cell is transfected with an siRNA which interacts with the siRNA tag of the transcript of the construct and brings about inhibition of expression of the target gene by means of RNA interference.

In an alternative embodiment, the eukaryotic cell into which the target gene is to be introduced may also be in the form of a lysate.

The method for inhibiting the expression of a target gene in at least one eukaryotic cell comprises the following steps according to the invention:

(a) provision of at least one eukaryotic cell, where the cell is capable of RNA interference,
(b) transfection of the at least one eukaryotic cell with at least one composition of the invention, and
(c) introduction of at least one siRNA which is complementary to an siRNA tag of a transfected construct, whereby expression of the target gene is inhibited.

Various possibilities are available for introducing the transcript of the target gene according to the invention into the cell. On the one hand, the cell can be transfected directly with a construct of the invention in the form of an RNA, for example of an mRNA, itself. On the other hand, the cell can also be transfected with a nucleic acid amplification product, for example PCR product, or nucleic acid fragment, in which case these have a promoter which brings about transcription of the mRNA of the target gene in the cell. The cell is preferably transfected with a vector, however, in which case the vector comprises a promoter which is active in the cell and brings about transcription of the target gene.

If the cell is transfected with a PCR product or a vector which comprise a promoter, in one embodiment the promoter is under the control of an effector. The effector-controlled promoter makes further control of expression possible.

The sequence of the siRNA tag employed according to the invention preferably comprises a sequence which is not known from eukaryotes. siRNA tags of the invention can therefore be derived from prokaryotes or represent artificial sequences which have no correspondence with known sequences from databases. The fact that the siRNA tags are not a constituent of the sequence of the target genes means that they are employable universally. A significant advantage is that the siRNA tags can be cloned at the level of DNA, in front of or behind each sequence coding for an mRNA or other functional sequence such as, for example, tRNA, rRNA, etc. Each siRNA tag thus represents a cassette which may be for example a component of a cloning vector.

A further advantage of the invention is that it is possible to accumulate experience about which siRNA tags bring about RNA interference particularly potently in which cells. Precisely these siRNA tags can then be employed repeatedly for different target genes.

FIG. 1A shows a fundamental scheme of the principle by which an siRNA leads, via a complementary siRNA tag fused to the target gene ("gene of interest"), to a reduction in the expression of the complete construct. FIG. 1B represents by way of example the detailed location of an siRNA tag in the 3' region of a gene construct coding for a protein. In this case, the siRNA tag was introduced between translation STOP codon signals and a poly-A signal in the 3'-untranslated region (3'UTR). An siRNA tag can in this case be a component of a larger DNA construct which comprises further functional genetic elements (protein tag for purification or detection of a protein, STOP codon sequences, poly-A signal sequences, etc.) and is cloned as transcription unit into the construct.

Three different DNA cassettes which, besides the siRNA tag sequence, also comprise further properties for cloning and subsequent expression of the recombinant products were designed in each case specifically for the three siRNAs validated by way of example (see FIG. 2). These DNA cassettes have cohesive ends for ligation into the intended vectors. A sequence coding for a His tag is present in the DNA cassettes in FIG. 2A for later detection of fusion proteins. By contrast, introduction of a His tag was dispensed with in the DNA cassettes depicted in FIG. 2B. The triple stop signal, and a polyadenylation signal, supplement the properties of the DNA cassette which are necessary for correct expression of the later gene construct.

FIG. 3 shows siRNA tag-mediated gene silencing of pEFGP constructs (plasmids coding for EGFP). HeLa S3 cells transfected with pEGFP constructs which comprise either the siRNA tag sequence No. 247 [SEQ ID NO:1], 1248 [SEQ ID NO:2] or 2904 [SEQ ID NO:3] (see Table 1), with or without the respectively complementary siRNAs (SEQ ID NO: 4, SEQ ID NO:5 and SEQ ID NO:6, respectively—see Table 1), were used. FIG. 3A and FIG. 3B are on the one hand fluorescence and transillumination photographs of the same section excited with light of the stated wavelength, and on the other hand phase contrast images for control purposes. The indicated clones are without His tag (FIG. 3A) or with His tag (FIG. 3B). FIG. 3C shows the immunological detection of the expression of constructs with His tag by means of detection of the His tag from lysates of transfected cells. When there is simultaneous cotransfection of the complementary siRNAs, gene silencing of the fusion proteins takes place. Cells transfected with pEGFP vector, and nontransfected cells, were used as controls.

FIG. 4 finally shows selective gene silencing by cotransfection of two expression plasmids with different siRNA tags and the respective siRNAs. Fluorescence and transillumination photographs of HeLa cells transfected with pDsRed 274, pEGFP 1248 and siRNAs of sequences 274 [SEQ ID NO:1] and 1248 [SEQ ID NO:2] (see Table 1). The images represent identical sections which had been excited with light of the wavelength indicated in each case.

The present invention describes an approach in which tag-specific siRNA molecules are employed for the specific gene inactivation (gene silencing) of transcripts without the need to design and prepare for an individual transcript, e.g. an mRNA or another functional RNA such as, for example, a tRNA, rRNA, etc., an siRNA specifically aimed thereat. The principle underlying this approach can be described as follows.

The DNA fragment coding for the functional RNA to be investigated can be cloned in a eukaryotic expression plasmid in order for example to make recombinant expression of an encoded protein possible or to discover the effects of a functional RNA. Fusion of a double-stranded DNA which comprises an siRNA tag for a specific siRNA in the reading frame of the functional RNA to be investigated makes gene inactivation of the functional RNA possible through cotransfection of this modified vector together with the specific siRNA. The double-stranded DNA molecule may, besides the recognition site for the siRNA (siRNA tag), include further specific properties such as, for example, coding sequences for short protein tags (e.g. His tag, Strep tag), STOP codons, polyadenylation signals or overhangs generated by restriction enzymes for direct cloning of the double-stranded molecule. This is depicted diagrammatically in FIG. 1.

The siRNA tags to be incorporated into the genetic construct are preferably derived from prokaryotic, particularly preferably from archae-bacterial gene sequences, which have a minimal, preferably no, homology with eukaryotic gene sequences. This minimizes the risk of the siRNA directed against the siRNA tag causing nonspecific effects. Prokaryotic gene sequences have proved to be particularly suitable for the siRNA tags of the invention, especially sequences from archae, for example from the genera *Thermotoga* (e.g. *Thermotoga maritima*, etc.), *Methanosarcina* (e.g. *Methanosarcina mazei*, etc.), *Pyrococcus* (e.g. *P. furiosus, P. horikoshii, P. woesei*, etc.), *Halobacterium* (e.g. *H. cutirubrum, H. denitrificans, H. halobium*, etc.), *Methanolobus* (e.g. *M. bombayensis, M. oregonensis, M. siciliae*, etc.), *Sulfolobus* (e.g. *S. acidocaldarius, S. brierleyi, S. hakonensis*, etc.) or *Acidilobus* (e.g. *A. aceticus*). Further corresponding archae genera are known to a person skilled in the art.

There are various bioinformatics methods for checking whether a particular prokaryotic sequence has homologies with a previously known eukaryotic sequence, such as, for example, a modified Smith-Waterman algorithm, which was employed in the present case.

For the experiments in the context of the present invention, three siRNAs were selected by way of example, which on the one hand offered a very high probability of arriving at the desired results, and which on the other hand showed according to the Smith-Waterman algorithm the smallest agreement with known eukaryotic genes. The function of these siRNAs was investigated by fusing synthetic, double-stranded (ds) DNA molecules which possess an appropriately complementary siRNA binding site (siRNA tag) to the 3' end of the EGFP expression cassette of an EGFP reporter plasmid (pEGFP-C1).

Three different DNA cassettes which, besides the siRNA tag sequence, also include further properties for cloning and subsequent expression of the recombinant products (see FIG. 2) were designed for each of the three siRNA molecules validated by way of example in the context of the present invention (see Table 1). These DNA cassettes have cohesive ends for ligation into the intended vectors. A sequence coding for a His tag is present for later detection of the fusion proteins for the DNA cassettes in FIG. 2A. On the other hand, no His tag was introduced in the DNA cassettes depicted in FIG. 2B. The triple STOP codon, and a polyadenylation signal supplement the properties of the DNA cassette which are necessary for correct expression of the later gene construct.

The DNA cassettes shown (see FIG. 2) were then cloned into the pEGFP-C1 expression plasmid which had been linearized using the restriction enzymes EcoRI and BamHI.

Recombinant clones were characterized by sequencing both the insert itself and the vector in the region of the boundaries of the insert.

After the molecular characterization of the recombinant pEGFP plasmid which expresses the RNAs with the siRNA tags, these constructs can be used for functional analysis of the appropriate siRNAs.

In a first experiment, all the constructs were used in transient transfection experiments in order to analyze the EGFP expression of each clone as indicator of the correct transcription and translation of the modified expression cassette. In order to check this HeLa S3 cells were transfected with the individual recombinant plasmids pEGFP-274 (coding for EGFP-siRNA tag SEQ ID NO:1), pEGFP-1248 (coding for EGFP-siRNA tag SEQ ID NO:2), and pEGFP-2904 (coding for EGFP-siRNA tag SEQ ID NO:3), and the EGFP expression was determined by fluorescence microscopy 48 hours after the transfection. Cotransfection of the DNA constructs together with the appropriate siRNA directed against the respective siRNA tag made functional characterization thereof possible. 48 hours after the cotransfection, the cells transfected with the DNA constructs and the specific siRNA showed a significant reduction in EGFP expression compared with the cells transfected with the plasmid alone (see FIG. 3a).

In the case of the genetic constructs which code for a C-terminal His tag fusion, correct expression of the EGFP-His fusion protein was investigated by Western blotting. HeLa S3 cells were transfected with the plasmids pEGFP-274-hs (coding for EGFP-His tag-siRNA tag SEQ ID NO:1), pEGFP-1248-hs (coding for EGFP-His tag-siRNA tag SEQ ID NO:2), pEGFP-2904-hs (coding for EGFP-His tag-siRNA tag SEQ ID NO:3) or pEGFP-C1 (initial plasmid without insert). Cotransfection of the DNA constructs together with the appropriate siRNA directed against the respective siRNA tag also made functional characterization thereof possible in this case. 48 hours after the cotransfection, the cells transfected with the DNA constructs and the specific siRNA showed a significant reduction in EGFP expression compared with the cells transfected with the plasmid alone (see FIG. 3b). In a further part of the experiment, the cells were lyzed 48 hours after the transfection, and the proteins were extracted and investigated by Western blotting using Penta-His monoclonal antibodies specific for the His tag to find whether they express the His tag. The EGFP-His fusion protein (with a molecular weight of about 28 kDa) was detectable only in cells transfected with recombinant EGFP constructs, whereas the fusion protein did not occur in nontransfected cells and in pEGFP-C1-transfected cells. Cotransfections of the individual pEGFP constructs with the siRNA directed against the respective siRNA tag led in each case to an efficient gene silencing effect (concerning this, see the Western blot shown in FIG. 3C).

One of the most important advantages of the system of the invention which employs tag-specific siRNA is the possibility of being able to use two or more siRNA tag-expressing constructs which are located on one or more vectors, for example plasmids, together with the appropriately functionally validated siRNAs. This system makes it possible for a plurality of recombinant genes to be coexpressed, and for each of these components to be switched off specifically by cotransfection with the appropriate siRNA.

An important experiment used to investigate the cotransfection of two siRNA tag-reporter constructs together with the respective tag-specific siRNAs directed at the expressed gene is depicted by way of example in FIG. 4. In order to investigate the gene silencing of one or simultaneously both plasmid constructs in parallel-transfected cells, HeLa cells were cotransfected with the plasmids pDsRed 274 (codes for DsRed-siRNA tag SEQ ID NO:1) and pEGFP 1248 (codes for EGFP-siRNA tag SEQ ID NO:2). In separate approaches, either a nonspecific control siRNA or one of the respectively specific tag-siRNAs (sequence 274, specific for siRNA tag SEQ ID NO:1, or sequence 1248, specific for siRNA tag SEQ ID NO:2) were transfected in addition with these two plasmids. In a further approach, both specific siRNAs were present together with the plasmids in the transfection mixture. It was possible by these experiments to demonstrate the specificity of the siRNA employed for the respective siRNA tag, which represents the basis for differential expression control in experiments. The cotransfections were analyzed with a fluorescence microscope after incubation for 48 hours.

As shown in FIG. 4, the reporter genes of both plasmid constructs are expressed in a cell despite cotransfection of a non-functional control siRNA (column A). The HeLa cells transfected with both plasmids show, even with simultaneous transfection of a control siRNA, parallel expression of the fluorescent proteins. On selective inhibition of DsRed expression by the siRNA with sequence 274 (specific for the siRNA tag SEQ ID NO:1, see Table 1), a large decrease in the fluorescence signal is evident; expression of the EGFP protein is meanwhile not impaired (column B). Conversely, selective inhibition of the EGFP protein by the siRNA with sequence 1248 (specific for the siRNA tag SEQ ID NO:2, see Table 1) is shown, without a reduction in the DsRed signal in this case (column C). Finally cotransfection of both plasmids with the respective specific siRNAs inhibits the expression of both reporter genes so strongly that virtually no fluorescence signals are now emitted by the cells (column D).

The invention claimed is:

1. A method for inhibiting the expression of a target gene in at least one eukaryotic cell capable of RNA interference, the method comprising:
   a) providing the at least one eukaryotic cell,
   b) transfecting the at least one eukaryotic cell with a composition comprising a genetic construct comprising
      the target gene, and
      an siRNA tag that forms a transcription unit together with the target gene, and
   c) introducing at least one siRNA which interacts with the siRNA tag of the transfected genetic construct to inhibit the expression of the target gene in the at least one eukaryotic cell,
   wherein the siRNA tag is selected from the group consisting of SEQ ID NO:1, SEQ ID NO:2 and SEQ ID NO:3.

2. The method as claimed in claim 1, wherein the at least one eukaryotic cell is in the form of a lysate.

3. The method as claimed in claim 1, wherein the siRNA is introduced into the at least one eukaryotic cell by means of a nucleic acid which codes for the siRNA, and wherein synthesis of the siRNA is under the control of a promoter.

4. The method as claimed in claim 3, wherein the promoter is under the control of an effector.

5. The method as claimed in claim 4, wherein the effector is transiently applied in order to bring about time-controlled synthesis of the siRNA.

6. The method as claimed in claim 1, wherein the siRNA comprises a sequence selected from the group consisting of SEQ ID NO:4, SEQ ID NO:5 and SEQ ID NO:6.

7. The method as claimed in claim 1 further comprising controlling inhibition of the target gene in a plurality of eukaryotic cells by sequential introduction of the siRNA.

8. The method as claimed in claim 1, wherein the composition is used for transient generation of different expression patterns in the at least one eukaryotic cell or in a plurality of eukaryotic cells.

9. The method as claimed in claim 1, wherein the expression of the target gene is reduced by at least 40%.

10. The method as claimed in claim 9, wherein the expression of the target gene is reduced by at least 70%.

11. The method as claimed in claim 10, wherein the expression of the target gene is reduced by at least 90%.

12. The method as claimed in claim 1, wherein the degree of inhibition of the expression of the target gene is determined by means of quantifying the signal of a fused marker gene.

13. The method as claimed in claim 1, wherein the transfection of the at least one eukaryotic cell takes place transiently.

14. The method as claimed in claim 1, wherein the at least one eukaryotic cell is stably transfected.

15. A method for inhibiting the expression of at least one target gene in a eukaryotic cell, the method comprising:
    transfecting the eukaryotic cell with a composition comprising
       a first genetic construct comprising
          a first target gene, and
          a first siRNA tag that forms a transcription unit together with the first target gene; and
       a second genetic construct comprising
          the first target gene or a second target gene: and
          a second siRNA tag that forms a transcription unit together with the first target gene or the second target gene; and
    introducing at least one of
       an siRNA which interacts with the first siRNA tag of the transfected first genetic construct to inhibit the expression of the first target gene, and
       an siRNA which interacts with the second siRNA tag of the transfected second genetic construct to inhibit the expression of the first target gene or the second target gene,
    wherein the first siRNA tag and the second siRNA tag are each selected from the group consisting of SEQ ID NO:1, SEQ ID NO:2 and SEQ ID NO:3, and
    wherein the first siRNA tag and the second siRNA tag differ in nucleic acid sequence.

16. The method as claimed in claim 15, wherein the first target gene and the second target gene differ in nucleic acid sequence.

17. The method as claimed in claim 15, wherein the first target gene represents a first allele and the second target gene represents a second allele of the same gene.

18. The method as claimed in claim 15, wherein the composition comprises a third genetic construct, wherein the third genetic construct comprises:
    the first target gene, the second target gene or a third target gene: and
    a third siRNA tag that forms a transcription unit together with the first target gene, the second target gene or the third target gene; and wherein the method further comprises introducing at least one of
- an siRNA which interacts with the first siRNA tag of the transfected first genetic construct to inhibit the expression of the first target gene,
- an siRNA which interacts with the second siRNA tag of the transfected second genetic construct to inhibit the expression of the first target gene or the second target gene, and
- an siRNA which interacts with the third siRNA tag of the transfected third genetic construct to inhibit the expression of the first target gene, the second target gene or the third target gene,
- wherein the third siRNA tag is selected from the group consisting of SEQ ID NO:1, SEQ ID NO:2 and SEQ ID NO:3, and
- wherein the third siRNA tag differs in nucleic acid sequence from the first siRNA tag and the second siRNA tag.

19. The method as claimed in claim 15, wherein at least one of the target genes is fused to a marker gene which makes it possible to detect the expression of a fusion protein expressed by the fused gene.

20. The method as claimed in claim 15, wherein both of the target genes are fused to a marker gene which makes it possible to detect the expression of fusion proteins expressed by the fused genes.

21. The method as claimed in claim 19, wherein the marker gene is selected from the group consisting of GFP, EGFP, YFP, CFP, dsRed, Myc tag, E tag, FLAG tag, Glu-Glu tag, GST tag, HA tag, His tag, HSV tag, luciferase, MBP, protein C tag, S tag, T7 tag, V5 tag, VSV-g tag, avidin/streptavidin/strep tag, thioredoxin, His-patch thioredoxin, β-galactosidase, chloramphenicol acetyltransferase, cellulose binding domains (CBDs), chitin binding domain, staphylococcal protein A, streptococcal protein G, neo, hyg, pac, zeo, gpt, ble, dhfr, hpt and npt II.

22. The method as claimed in claim 19, wherein the marker gene codes for a fluorescence-generating protein.

23. The method as claimed in claim 1, wherein the at least one eukaryotic cell is of animal origin.

24. The method as claimed in claim 23, wherein the at least one eukaryotic cell is a mammalian cell.

25. The method as claimed in claim 1, wherein the at least one eukaryotic cell is of vegetable origin.

26. The method as claimed in claim 1, wherein the at least one eukaryotic cell is of mycotic origin.

27. The method as claimed in claim 26, wherein the at least one eukaryotic cell is a yeast cell capable of RNA interference.

28. The method as claimed in claim 15, wherein the eukaryotic cell is in the form of a lysate.

29. The method as claimed in claim 1, wherein the siRNA tag is a constituent of a promoter, enhancer or silencer.

30. The method as claimed in claim 1, wherein the siRNA tag is located downstream or upstream of the target gene or overlaps with the target gene.

31. The method as claimed in claim 1, wherein the siRNA tag is located in an intron of the target gene or overlaps with an intron.

32. The method as claimed in claim 1, wherein the genetic construct includes a protein tag fused to the target gene for protein purification.

33. The method as claimed in claim 32, wherein the protein tag for protein purification is selected from the group consisting of His tag, HA tag, ERK tag, GFP and related fusion tags, Myc tag, FLAG tag, GST tag, Strep tag, β-Gal tag and MBP tag.

34. The method as claimed in claim 1, wherein the genetic construct is located on a vector.

35. The method as claimed in claim 15, wherein the first genetic construct and the second genetic construct are located on two different vectors.

36. The method as claimed in claim 15, wherein the first genetic construct and the second genetic construct are located on one vector.

37. The method as claimed in claim 34, wherein the vector is a plasmid.

38. The method as claimed in claim 34, wherein the vector is a transposon.

39. The method as claimed in claim 34, wherein the vector is a virus.

40. The method as claimed in claim 1, wherein the genetic construct is a constituent of a PCR product.

\* \* \* \* \*

SEQUENCE LISTING

<160> NUMBER OF SEQ ID NOS: 9

<210> SEQ ID NO 1
<211> LENGTH: 21
<212> TYPE: DNA
<213> ORGANISM: Artificial
<220> FEATURE:
<223> OTHER INFORMATION: siRNA-Tag Sequence

<400> SEQUENCE: 1
cagggtatcg acgattacaa a                                              21

```
<210> SEQ ID NO 2
<211> LENGTH: 21
<212> TYPE: DNA
<213> ORGANISM: Artificial
<220> FEATURE:
<223> OTHER INFORMATION: siRNA-Tag Sequence

<400> SEQUENCE: 2
aagcgttgaa atagcgtaca a                                              21

<210> SEQ ID NO 3
<211> LENGTH: 21
<212> TYPE: DNA
<213> ORGANISM: Artificial
<220> FEATURE:
<223> OTHER INFORMATION: siRNA-Tag Sequence

<400> SEQUENCE: 3
ctggatacgc gggacgttta a                                              21

<210> SEQ ID NO 4
<211> LENGTH: 19
<212> TYPE: RNA
<213> ORGANISM: Artificial
<220> FEATURE:
<223> OTHER INFORMATION: sense strand of siRNA sequence with a UU
      overhang at the 3'-end

<400> SEQUENCE: 4
ggguaucgac gauuacaaa                                                 19

<210> SEQ ID NO 5
<211> LENGTH: 19
<212> TYPE: RNA
<213> ORGANISM: Artificial
<220> FEATURE:
<223> OTHER INFORMATION: sense strand of siRNA sequence with a dTT-
      overhang at the 3'-end

<400> SEQUENCE: 5
gcguugaaau agcguacaa                                                 19

<210> SEQ ID NO 6
<211> LENGTH: 19
<212> TYPE: RNA
<213> ORGANISM: Artificial
<220> FEATURE:
<223> OTHER INFORMATION: sense strand of siRNA sequence with a UU
      overhang at the 3'-end

<400> SEQUENCE: 6
ggauacgcgg gacguuuaa                                                 19

<210> SEQ ID NO 7
<211> LENGTH: 19
<212> TYPE: RNA
<213> ORGANISM: Artificial
<220> FEATURE:
<223> OTHER INFORMATION: anti-sense strand of siRNA sequence with a
      GU-overhang at 3'-end

<400> SEQUENCE: 7
uuuguaaucg ucgauaccc                                                 19

<210> SEQ ID NO 8
<211> LENGTH: 19
<212> TYPE: RNA
<213> ORGANISM: Artificial
```

```
-continued

<220> FEATURE:
<223> OTHER INFORMATION: anti-sense strand of siRNA sequence with a
      dTT- overhang at the 3'-end

<400> SEQUENCE: 8
uuguacgcua uuucaacgc                                                    19

<210> SEQ ID NO 9
<211> LENGTH: 19
<212> TYPE: RNA
<213> ORGANISM: Artificial
<220> FEATURE:
<223> OTHER INFORMATION: anti-sense strand of siRNA sequence with a
      GA-overhang at 3'-end

<400> SEQUENCE: 9
uuaaacgucc cgcguaucc                                                    19
```